United States Patent
Ganga, Sr.

(10) Patent No.: US 10,238,686 B1
(45) Date of Patent: *Mar. 26, 2019

(54) ANTIMICROBIAL SKIN CREAM

(71) Applicant: Yvon Samba Ganga, Sr., San Diego, CA (US)

(72) Inventor: Yvon Samba Ganga, Sr., San Diego, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 15/614,967

(22) Filed: Jun. 6, 2017

Related U.S. Application Data

(63) Continuation-in-part of application No. 15/133,172, filed on Apr. 19, 2016, now Pat. No. 9,987,305, and a continuation-in-part of application No. 15/363,940, filed on Nov. 29, 2016, now Pat. No. 10,105,298.

(51) Int. Cl.

| | | |
|---|---|---|
| *A61K 36/00* | (2006.01) | |
| *A61K 33/06* | (2006.01) | |
| *A61K 31/255* | (2006.01) | |
| *A61K 31/185* | (2006.01) | |
| *A61K 33/00* | (2006.01) | |
| *A61K 31/045* | (2006.01) | |
| *A61K 33/04* | (2006.01) | |
| *A61K 38/01* | (2006.01) | |
| *A61K 35/06* | (2006.01) | |
| *A61K 36/63* | (2006.01) | |
| *A61K 36/61* | (2006.01) | |
| *A61K 36/82* | (2006.01) | |
| *A61K 33/12* | (2006.01) | |
| *A61K 35/644* | (2015.01) | |
| *A61K 36/886* | (2006.01) | |
| *A61K 31/355* | (2006.01) | |
| *A61K 31/59* | (2006.01) | |
| *A61K 31/375* | (2006.01) | |
| *A61K 31/525* | (2006.01) | |
| *A61K 31/197* | (2006.01) | |
| *A61K 31/4188* | (2006.01) | |
| *A61K 31/675* | (2006.01) | |
| *A61K 33/34* | (2006.01) | |
| *A61K 33/24* | (2019.01) | |
| *A61K 33/26* | (2006.01) | |

(52) U.S. Cl.
CPC ............ *A61K 33/06* (2013.01); *A61K 31/045* (2013.01); *A61K 31/185* (2013.01); *A61K 31/197* (2013.01); *A61K 31/255* (2013.01); *A61K 31/355* (2013.01); *A61K 31/375* (2013.01); *A61K 31/4188* (2013.01); *A61K 31/525* (2013.01); *A61K 31/59* (2013.01); *A61K 31/675* (2013.01); *A61K 33/00* (2013.01); *A61K 33/04* (2013.01); *A61K 33/12* (2013.01); *A61K 33/24* (2013.01); *A61K 33/26* (2013.01); *A61K 33/34* (2013.01); *A61K 35/06* (2013.01); *A61K 35/644* (2013.01); *A61K 36/61* (2013.01); *A61K 36/63* (2013.01); *A61K 36/82* (2013.01); *A61K 36/886* (2013.01); *A61K 38/014* (2013.01)

(58) Field of Classification Search
None
See application file for complete search history.

(56) References Cited

U.S. PATENT DOCUMENTS

| | | | | |
|---|---|---|---|---|
| 2002/0106337 | A1* | 8/2002 | Deckers | A23D 7/001 424/59 |
| 2010/0178511 | A1* | 7/2010 | Letard | C07F 15/025 428/404 |

FOREIGN PATENT DOCUMENTS

DE        10145833 A1 *   3/2003      ............... A61K 8/97

OTHER PUBLICATIONS

Angienda et al, Potential application of plant essential oils at sub-lethal concentrations under extrinsic conditions that enhance their antimicrobial effectiveness against pathogenic bacteria. African Journal of Microbiology Research (2010), vol. 4, No. 16, pp. 1678-1684.*

* cited by examiner

*Primary Examiner* — Qiuwen Mi
(74) *Attorney, Agent, or Firm* — Plager Schack LLP; Mark H. Plager; Kara K. Verryt

(57) ABSTRACT

A cream for treating the skin may include gray clay kaolin; sodium lauryl ether sulfate; blue tartrazine; sodium chloride; menthol; metabisulfite sodium; gelatin; mineral oil; olive oil; oil of cloves; water; green tea; honey; talc; and aloe vera. The cream may also include apple perfume, vitamin E, vitamin D, vitamin C, vitamin B2, vitamin B5, vitamin H, vitamin B6, and vitamin D. The cream may also include fatty acids.

10 Claims, No Drawings

ANTIMICROBIAL SKIN CREAM

RELATED APPLICATION

This application claims priority to and is a continuation of non-provisional patent application U.S. Ser. No. 15/133,172 filed on Apr. 19, 2016 and U.S. Ser. No. 15/363,940 filed on Nov. 29, 2016, the entire contents of each of which is herein incorporated by reference.

BACKGROUND

The embodiments herein relate generally to skin care, and more particularly, to an antimicrobial skin cream.

The skin is the largest organ in the body, covering the surface of the human body and serving as the first line of defense in protecting the human from invasion of foreign pathogens and external injuries. In terms of wound healing, a human has the ability to self-heal a small area. However, when a person has a large area wound or poor skin restoration ability, such as those affected by diabetes, psoriasis, or leprosy, the individual may be unable to self-heal adequately, which can lead to infection.

Therefore, what is needed is a skin cream designed to improve tissue regeneration, particularly when treating skin lesions, wounds, burns, and Buruli ulcers while simultaneously having cosmetic applications as well.

SUMMARY

Some embodiments of the present disclosure include a cream for treating the skin. The cream may include gray clay kaolin; sodium lauryl ether sulfate; Brilliant blue or blue tartrazine; sodium chloride; menthol; metabisulfite sodium; gelatin; mineral oil; olive oil; oil of cloves; water; green tea; honey; and aloe vera. The cream may also include talc, apple perfume, vitamin E, vitamin D, vitamin C, vitamin B2, vitamin B5, vitamin H, vitamin B6, and vitamin D.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The cream of the present disclosure may be used to heal and rejuvenate the skin and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

1. Gray clay kaolin
2. Sodium lauryl ether sulfate
3. Sodium chloride
4. Menthol
5. Water
6. Honey
7. Aloe Vera
8. Vitamins
9. Gelatin
10. Mineral Oils
11. Metabisulfite Sodium
12. Talc
13. Green Tea
14. Brilliant Blue or Blue Tartrazine The various elements of the cream of the present disclosure may be related in the following exemplary fashion. It is not intended to limit the scope or nature of the relationships between the various elements and the following examples are presented as illustrative examples only.

By way of example, some embodiments of the present disclosure include a skin cream comprising gray clay kaolin (chemical formula $Al_2Si_2O_5(OH)_4$); sodium lauryl ether sulfate; $CH_3(CH_2)_{11}(OCH_2CH_2)_nOSO_3Na$, wherein n is 2 or 3; blue tartrazine (chemical formula $C_{16}H_9N_4Na_3O_9S_2$); salt (NaCl); menthol ($Co_{10}H_2O$); metabisulfite sodium ($Na_2S_2O_5$); gelatin; mineral oil ($C_{102}H_{151}O_{39}N_{31}$); olive oil ($CH_3(CH_2)_7CH=CH(CH_2)_7COOH$); oil of cloves

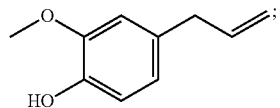

water; talc ($Mg_3Si_4O_{10}(OH)_2$); green tea (*camellia sinensis*, which has anti-oxidant and anti-inflammatory properties and may enhance wound healing); perfume, such as apple scented perfume; honey; aloe vera; optionally, oleic acid; optionally, benzoic acid; and optionally a mixture of vitamins. The fatty acids (oil of cloves, benzoic acid, and oleic acid) may have antimicrobial properties. In some embodiments, the mixture of vitamins may comprise vitamin E; vitamin D; vitamin C; vitamin B2; vitamin B5; vitamin H; vitamin B6; and vitamin D. Gray clay kaolin is a hydrous aluminum phyllosilicate and may include mineral elements, such as Fe, Mg, Na, K, Ti, Ca, and water. The $CH_3(CH_2)_{11}(OCH_2CH_2)_nOSO_3Na$ may provide for excellent decontamination, emulsification, dispersion, wetting, solubilizing performance and foaming. It may also function as a thickener with good solvency, while also having limited irritation to skin and eyes. The skin cream may have a pH of about 7.4. Additionally, the skin cream may be green in color.

A particular embodiment of the present disclosure may comprise a batch of the cream comprising about 260 kg gray kaolin clay, about 4 kg sodium lauryl ether sulfate, about 0.8 oz (or 25 g) blue tartrazine; about 2.2 kg salt (sodium chloride—NaCl), about 100 g menthol; about 50 g metabisulfite sodium; about 95 kg gelatin; about 20 L mineral oil; about 25 L olive oil; about 25 L oil of cloves; about 20 L water; about 20 kg talc; about 5 L green tea; about ⅛ L perfume; about 5 L honey; about 10 L aloe vera; about 2,000 international units (IU) vitamin E; about 100,000 IU vitamin A; about 300 mg vitamin C; about 100 mg vitamin B2; about 250 mg vitamin B5; about 2.5 mg vitamin H; about 100 mg vitamin B6; and about 400 IU vitamin D. In embodiments, the cream may comprise about 60% gray kaolin clay.

The gray clay kaolin may comprise alumina silicate, calcium, magnesium, sodium, and potassium. The high silica content of the clay may result in the strengthening of the elastic tissues on the body, particularly in the case of contaminated blood.

The gelatin used in forming the cream of the present disclosure may be comprised mainly of collagen, which is a protein found in animal tissues, ligaments, tendons, bone, and skin. Thus, the gelatin may have healing properties, because it is a rich source of dietary collagen. The gelatin may also comprise proline, which is an amino acid that may help maintain a youthful appearance. Moreover, the gelatin may also contain Zn, Cu, and Ca.

The Brilliant blue or blue tartrazine used in the cream may be a product derived from synthetic lemon yellow and is conventionally used as a food coloring.

The mineral oil included in the cream of the present disclosure may prevent water loss from the skin. In other words, it may act as a moisturizer. In some embodiments, the mineral oil may be replaced by Vaseline. The use of mineral oil may lead to an increase in stratum corneum content by reducing trans epidermal and emolliency.

To summarize, the skin cream of the present disclosure may comprise the following:
Part 1: Gray clay kaolin
$Al_2(Si_2O_5)(OH)_4$
All elements listed in formula:
Al, H, O, Si—search for minerals with similar chemistry
Common Mineral Elements: Fe, Mg, Na, K, Ti, Ca, $H_2O$
The gray clay Kaolin formula is: $(Ca,Na,H)(Al,Mg,Fe,Zn)_2(Si,Al)_4O_{10}(OH)_2*H_2O$+sodium lauryl ether sulfate (shown below)

where n is 2 or 3.
Part 2: sodium laureth sulfate: $CH_3(CH_2)_{10}CH_2(OCH_2CH_2)OSO_3Na$
Part 3: water, which naturally contains minerals, such as Mg, Na, Ca, Fe, and the like
Part 4: Brilliant Blue ($C_{37}H_{34}N_2Na_2O_9S_3$) or blue tartrazine ($C_{16}H_9N_{43}O_9S_2$):

Final Product: $(Al,Zn,Fe1,67MgO,33)Si_4O_{10}(H)_2Na^+Ca^{++}$)

The weak acid character of the green clay as a Bronsted character clay arises mainly due to the dissociation of the intercalated water molecules coordinated to lauryl ether sulfate and Brilliant blue or blue tartrazine. Higher levels of Bronsted acidity are achieved when highly polarizing ions in solution have exchanged for $Na^+$, $Ca^{2+}$, in the natural clay, ions $Na^+$ present in laureth sulfate and blue tartrazine with alkali properties:

$[M(H_2O)_n]^{3+}+\Leftrightarrow[M(H_2O)_n-1OH]^{2+}+H^+$(green cream clay pH=7.4)

The surface area and the pore volume in the green cream clay structure may also add to the efficiency of the catalyst.

Total acidity may be further increased by proton-exchange on treating the gray clay with water, sodium laureth sulfate, and brilliant blue or blue tartrazine. As a result, a corrosive acid medium is avoided, and the clay is used as a Bronsted acid.

The interlayer in the antimicrobial green clay normally contains $Na^+$, $Ca^{2+}$, and $Mg^{2+}$ that are alkali properties as compensatory cations for the charge imbalance. When the clay is dry, these cations reside in the hexagonal cavities of the silica layers. However, when the clay is treated with water, lauryl ether sulfate, and blue tartrazine, the cations may relocate themselves in the interlamellar region and become exchangeable by a variety of both metallic and nonmetallic cations, such as $H_3O^+$, $Al^{3+}$, $Fe^{3+}$ and the like.

The synthesis of the green antimicrobial cream is summarized, in detail, as follows:
Step 1: sodium lauryl ether sulfate $(CH_3(CH_2)_{10}((CH_2)O)_nSO_3Na$, where n is 2 or 3
Step 2: water containing natural minerals, such as Mg, Na, Ca, Fe, Zn, Cu, K, Mn, and the like; talc containing Mg, Mn, Ti, Fe, and Ca; and gelatin containing Zn, Cu, and Ca.
Step 3: Brilliant Blue: $C_{37}H_{34}N_2O_9S_3$, wherein Brilliant Blue is a food colorant
Step 4: 2.2 kg of NaCl, the amount of which may vary depending on the use (cosmetic vs. skin infection). In this step, the solution may be blue in color.
Step 5: adding the ingredients of Steps 1-4 together with gray clay Kaolin, which has the following formula:

$(Ca,Na,H)(Al,Mg,Fe,Zn)_2(Si,Al)_4O_{10}(OH)_2*H_2O$

After mixing the ingredients, the gray color will change to green, wherein the final product is the antimicrobial green clay cream having the following formula:

$(Al,Zn,Fe_1,67MgO_{33})Si_4O_{10}(OH)_2Na^+Ca^{++}$

Processing the above by mechanical energy, i.e. by stirring and kneading the composition, results in:

$(Al,Zn,Fe+++,Fe++,67MgO_{33})Si_4O_{10}(OH)_2Na^+Ca^{++}$

Thus, the final product after stirring and kneading, which activates the hydrophilic property of the cream, is:

$(Al,Zn,Fe^{+++},Fe^{++},MgO,Mn,Cu^{++},Cu^+,Ti,Mo+)Si_4O_{10}(OH)_2K^+Na^+Ca^{++}$ wherein the structural formula is described by the following:
interlayer position: $Na^+$, $Ca^{2+}$, $K^+$, $H_3O^+$
tetrahedral layers: Si, Al
octahedral layers: Al, $Fe^{3+}$, $Fe^{2+}$, Mg, Mn, Zn, $Cu^{2+}$, $Mo^+$, Ti.

The following crystalline oxides may have the following position in the antimicrobial cream of the present disclosure:
$SiO_2$: octahedral and $SiO^-$, $SiO_4$, wherein the amount of silicon in the final composition is about 55-65% by mass
$Al_2O_3$: tetrahedral and $AlO^-$, AlOH, AlOOH position, wherein the amount of aluminum in the final composition is about 7-27% by mass
$Fe_2O_3$: FeOOH, wherein the amount of iron in the final composition is about 10 to about 20% by mass
other oxides represent about 25% by mass of the final composition
$Na_2O^+K_2O$: octahedral
NaCl: octahedral
$ZnCl_2$, CuCl: ½ tetrahedral
$TiO_2$: octahedral
ZnO: tetrahedral
MnO: octahedral is solid crystal, $Mn^{2+}$ is a liquid CuO$_2$: octahedral
CuO: octahedral
K$_2$O: octahedral In the composition of the present disclosure, the cations may be fixed on the surface of the colloids. Thus, the cream of the present disclosure has negatively charged surfaces between the layers described above, where the cations can be fixed. The bivalent ions (Ca$^{2+}$, Mg$^{2+}$, Mn$^{2+}$, Fe$^{2+}$) may be retained and attached on the negative inorganic colloid more strongly than the monovalent ions (Na$^+$, K$^+$). In other words, the cations may be fixed on the surface of the inorganic negative colloid. The lower hydrated ions may be more easily fixed than the strongly hydrated ions. The sodium cations of lauryl ether sulfate, which may be active in the surfactant, may exchange with the cations contained in the antimicrobial cream, causing salts to precipitate out. The salts may include calcium coceth sulfate, potassium coceth sulfate, magnesium coceth sulfate, copper coceth sulfate, manganese coceth sulfate, and zinc coceth sulfate, the structures of which are shown below.

In more detail, during Step 5 the green clay reacts as Bronsted character, and the materials react to the balance and stability of every element in an antimicrobial concept. The hydrogen protons (H$^+$) are attracted to the negatively charged clay surface to varying degrees, as shown below:

$$[M(H_2O)_n]^{3+} \leftrightarrow [M(H_2O)_n\text{-}1OH]^{2+}+H^+, \text{ where green cream clay has a pH of 7.4}$$

Thus, the change to a green color is caused by the transformation of Fe$^{2+}$ to Fe$^{3+}$+e. In other words, the color of the product, the antimicrobial clay, is green because of the combination of the two forms of iron. Thus, the antimicrobial green clay is the product of mixed valence condition of formation. The iron is reduced from Fe$^{3+}$ and enters into a silicate mineral structure. In general, iron would rather be an oxide when it is in the trivalent state, at which time it is reduced to the divalent state under the surface or near the surface. The silicate, sulfide, or carbonate hides when the silicate is oxidized, and the iron begins to group together in oxide clumps, eventually exiting the silicate structure. The production of trivalent oxidized iron typically results in a yellow, brown, or orange color. However, with the presence of Brilliant Blue or Blue Tartrazine, the color becomes green. The resulting final product has the following chemical structure: (Al,Zn,Fe1,67MgO,33)Si$_4$O$_{10}$(OH)$_2$Na$^+$Ca$^{++}$).

Summary of the Chemical Changes During Synthesis:

The Kaolin clay has a chemical formula of (Ca,Na,H)(Al, Mg,Fe,Zn)$_2$(Si,Al)(OH)$_2$nH$_2$O, wherein n is 2 or 3. The clay is treated with water and lauryl ether sulfate. As a result, the cations may relocate themselves in the interlamellar region and become exchangeable by a variety of both metallic and non-metallic ions (e.g., H$_3$O$^+$, Al$^{3+}$, Fe$^{3+}$), where this is shown below:

$$Al^{3+}(aq)+H_2O \rightarrow Al(OH)^{2+}+H^+$$

$$Al(OH)^{2+}+H_2O \rightarrow Al(OH)_2^{+}+H^+$$

$$Al(OH)_2^{+}+H_2O \rightarrow Al(OH)_3+H^+(aq)$$

Thus, the following reactions take place:

$$Al^{3+}+3H_2O \leftrightarrow Al(OH)_3+3H^+(aq)$$

$$Fe^{3+}+3H_2O \leftrightarrow Fe(OH)_3+3H^+(aq)$$

$$Mg^{2+}+2H_2O \leftrightarrow Mg(OH)_2+2H^+(aq)$$

The presence of H$^+$ and Cl$^-$ results in the formation of HCl which causes, for example, the following:

$$Mg(OH)_2(s)+2HCl \rightarrow MgCl_2(aq)+2H_2O(l)$$

The presence of Ca$^{2+}$ and OH$^-$ results in the formation of Ca(OH)$_2$, which results in, for example, the following:

$$MgCl_2(aq)+Ca(OH)_2(aq) \rightarrow Mg(OH)_2(aq)+CaCl_2(aq)$$

The presence of Na$^+$ and Cl$^-$ results in the formation of NaCl, which results in the following reactions:

$$Al(OH)_3+3Na^+(aq)+3Cl^-(aq) \rightarrow AlCl_3(s)+3Na^+(aq)+3OH^-(aq)$$

$$Fe(OH)_3+3Na^+(aq)+3Cl^-(aq) \rightarrow FeCl_3(s)+3Na^+(aq)+3OH^-(aq)$$

$$Mg(OH)_2+2Na^+(aq)+2Cl^-(aq) \rightarrow MglCl_2(s)+2Na^+(aq)+OH^-(aq)$$

$$H_3O^++OH^- \leftrightarrow H_2O(l), \text{ wherein the pH=7.4}$$

The above reactions may be activated with mechanical energy, and the formation of FeCl$_3$ may add a yellow coloring to the composition.

Brucite, which is a hydroxide of magnesium (Mg(OH)$_2$) is made up of octahedral magnesium hydroxide that stacks on top of one another. The overall charge of the molecule is zero.

Another basic structure is the structure of the gibbsite leaflets (Al$_2$(OH)$_6$), wherein the aluminum atoms replace the magnesium atoms. This results in a charge surplus because Mg$^+$ is replaced by Al$^{3+}$, resulting in dioctaedric and trioctaedric structures, which means that there are two or three cations, respectively, in the octahedral sites that occupy the aluminum and magnesium atoms in gibbsite and brucite. The negatively charged tetrahedral layers may be bonded by cation layers, such as Mg$^{2+}$ and Al$^{3+}$, which have a coordination of 6 and are thus located at quasi-regular octahedron centers. As a result, the tetrahedral layer is followed by an octahedral layer, and these two layers have the 4 oxygen atoms of the tetrahedral and the 2 oxyhydriles in common. The elementary mesh (a=0.52 nm, b=0.9 nn) contains size octahedral cavities, which occupy bivalent ions, such as Mg$^{2+}$. Under these conditions, the layer is called trioctahedral. At the same time, two thirds of these cavities are occupied by trivalent ions, such as Al$^{3+}$, and the layer is called dioctahedral.

Criteria for the Microscopic Structure of Clays

Important criteria of the clays are position, nature and degree of substitution, position, and nature of the interlayer load and the relocation of the load throughout the layer. A swelling occurs in the interlayer space as a result of the presence of water, lauryl ether sulfate, and mechanical energy in the antimicrobial product. Specifically, two swellings may occur: (1) a crystalline swelling; and (2) an osmotic swelling after and during the mixing using mechanical energy. For the other cations, meaning all other cation oxides other than the oxide cations of Al$^{3+}$ and Si$^{4+}$, only the crystalline swelling is observed.

As a result, the following trends are observed. The moisture content tends to reduce the dry unit weight, because water lauryl ether sulfate, and fatty acids take up the space that would have occupied the water particles. The component (water, lauryl ether sulfate, fatty acid) at which the maximum dry unit weight is attained forms the antimicrobial cream of the present disclosure. As isomorphic substitution, which is the replacement of one atom by another of similar size, may assist the above phenomena without disrupting the crystal structure of the embodiments. For example, iron oxides can be easily substituted by cations of neighboring ionic radii, such as Al, Mn, Cu, and Ti, without modifying the structure and, thus, while developing little permanent change. Fe(III) is present in hematite, goethite, or ferruhidride crystalline forms and in an amount of about 46% by mass. However, other cations ($Mn^{2+}$, $Zn^{2+}$, $Cu^+$, $Cu^{2+}$, $Mg^{2+}$, $Ti^{4+}$, $Al^{3+}$, and $Mo^+$) may be incorporated into the structure of the oxide.

Iron oxides, which are finely divided minerals have a size of from about 10 to 100 amstrong (a), may be the main source of metal. In comparison, aluminum oxides are very unaffected by $Al^{3+}$ substitutions and are large in size. Thus, they do not develop permanent loads and little variable load. The oxides of iron and aluminum are positively charged and exhibit strong pHzpc, wherein pHzpc is the pH of zero point of charge and corresponds to the pH value at which the surface of the solid is considered to be neutral Manganese oxides are scarce in the composition of the present disclosure and are very complex from a mineralogical point of view. They have a more diverse octahedral arrangement and composition than iron and aluminum oxides with, for example, octahedral layers containing aluminum and lithium, layered structures or tunnels that contain large cations ($K^+$), and the capacity to exchange cations to fix various metallic trace elements (Cu, Zn, Ni) having pHzpc values around 5 to 7. The fixation of metals can exceed the exchange capacity of the manganese oxide by incorporating metal, such as cobalt, into the crystal lattice.

In the composition of the present disclosure, the minerals are subject to substitutions for two reasons: (1) the presence of Brilliant blue and lauryl ether sulfate; and (2) coprecipitation of ions of the lower valences within the crystalline mesh ($Al^{3+}/Fe^{2+}$ or $Mg^{2+}Si^{4+}$, $Al^{3+}$), which allows the ions to develop a permanent load. The inorganic colloid surface charge may thus be permanent (isomorphic substitution). The inorganic colloids container in the antimicrobial cream of the present disclosure may thus participate in specific or non-specific absorption reactions allowing the fixing of cations.

The participation in the absorption reaction may be varied by the functional ionization of surfaces or ion absorption, degrees of solubility of iron oxides containing antimicrobial cream under crystallinity conditions, and their formation conditions in the Kaolin phase.

The compounds may be distinguished as gibbsite (Al (OH)$_3$), goethie (FeOOH), hematite (FeO$_3$), and poorly crystallized compounds (AlOOH, BOCHNITE). The antimicrobial cream of the present disclosure may possess permanent changes, however, in the SiOH and AlOH groups, wherein the angles of the associated crystals release additional negative charges (SiO$^-$, AlO$^-$). (AlSiO$_4$)$^-$ and (SiO$_2$) may also be present and may provide stability in a biological environment.

Isomorphic substitution may occur in the tetrahedral layers ($Si^{4+} \rightarrow Al^{3+}$, $Fe^{3+}$) or in the octahedral layers ($Al^{3+} \rightarrow Mg^{2+}Fe^{2+}$ or $Mg^{2+} \rightarrow Li^{2+}$). The substitutions may result in a load deficit, which may be expensed outside the loads.

When fatty acids, water, lauryl ether sulfate, and gelatin are added to the composition, they act as softening agents on the clay particles and move into a densely packed position, which requires mechanical energy. The interlayer boding between the tops of the silica layers is mainly due to Van der Waals attractions and other ion bonding, such as: interlayer position (Na$^+$, Ca$^{2+}$, H$_3$O$^+$); tetrahedral (Al, Si); and octahedral ($Al^{3+}$, $Fe^{2+}$, $Fe^{3+}$, $Cu^+$, $Cu^{2+}$, $Mg^{2+}$, $Zn^{2+}$, $Mn^{2+}$, $Mo^+$, $Ti^{4+}$). Thus, the bonding strength is weak, along with being softened by the water, lauryl ether sulfate, and fatty acid.

Therefore, the amount exchangeable ions from of water, lauryl ether sulfate, and fatty acids may be easily separated. The water, fatty acids, and lauryl ether sulfate may swell the clay because of the affinity for water. As a result, the cream may be susceptible to substantial volume change as a result of the swelling. The swelling may be caused by water gaining entry into the lattice structure, which may then shrink if the water, lauryl ether sulfate, or fatty acids are removed. The total energy between the particles may decrease as they approach each other.

Throughout the present disclosure, the notation (Na, Ca) means that Na and Ca are present in the same crystal sites in varying proportions. Simultaneous (Si, Al) replacement ensures that the elements remain in their normal oxidation states. However, even the formulas disclosed herein are approximate, as several other elements may be present.

In the antimicrobial cream of the present disclosure, the position of the exchangeable cations is not able to be determined precisely, because they can pass from one host site (hexagonal site) to another depending on the relative humidity, lauryl ether sulfate, fatty acids, and energy conditions to which they are subjected. The notion of host sites makes sense only as long as the cation remains bound to the clay surface. The movement of the cations may be followed by measurements of electrical conductivity. When the cations are hydrated, the layers may be sufficiently spread apart to allow the cations to pass from one site to another, and an electric current may be measured. The current may be a function of the compensating cation and the interactions between the clay surface and the cation. However, there may also be an electric current that generally remains ascribed to the compensating cations, although generally the clay of the present disclosure is described as frozen for the dry state.

Use of the Product for Skin Regeneration:

In the regeneration process of skin, calcium may be very important. Calcium has an established role in the homeostasis of mammalian skin and serves as a modulator in Keratinocyte proliferation and differentiation. Gradients of calcium concentrations increasing from 0.6 mM in the basal layer to >1.4 mM in the stratum granulosum are consistent with migration patterns in response to minor abrasions (normal wear). Dermal fibroblasts require calcium, but are approximately 100 times less sensitive than Keratinocytes. Normal calcium metabolism in the skin is dependent on cell membrane and cytosolic calcium binding proteins (calmodulin, cadherins, etc.). In wound repair, calcium is predominantly involved as Factor IV in the hemostatic phase, but it is expected to be required in epidermal cell migration and regeneration in later stage healing. Calcium is a potential central regular in wound healing. Also, a sustained elevated intracellular calcium (Ca$^{2+}$) concentration has thus emerged as a universal and require characteristic of activated cells. Activation of stem cells by Ca$^{2+}$ was accomplished by the use of the antimicrobial green clay cream of the present disclosure.

In the antimicrobial cream of the present disclosure, the role of Ca$^{2+}$ in stem cell activation suggests that the cells use the intracellular Ca$^{2+}$ concentration as a gauge to respond dynamically to the multitude of signals vying for their attention. Stem cells may adjust their proliferation activity in response to a wider variety of Ca$^{2+}$ signals. Thus, the extra concentration of calcium may emerge as a master regulator of stem cell activity. In other words, the Ca$^{2+}$ level in the antimicrobial cream may regulate stem cell activity (such as L-glutamate activity) by triggering a sustained increase of Ca$^{2+}$ within the cell. It should be noted that this change is not limited to the response to L-glutamate.

In the process of healing a wound or burn with the antimicrobial cream, the cells may acquire the molecules and ions needed from the area surrounding the cells. Thus, there may be an increased traffic of molecules and ions in and out of the cells through their plasma membrane. In healing wounds and skin regeneration, two problems should be considered:
  (1) Relative concentrations of molecules and ions, and ions moving spontaneously down their concentration gradient diffusion
  (2) Lipid layers are impermeable to most essential molecules and ions. The bilayers are permeable to water molecules and few other small, uncharged molecules, like oxygen ($O_2$) and carbon dioxide ($CO_2$, which may diffuse into or out of the cells through the plasma membrane in a process referred to as osmosis. However, lipid bilayers are impermeable to $K^+$, $Na^+$, $Ca^{2+}$, $Cl^-$, and $HCO_3^-$.

Small hydrophilic molecules, such as glucose, and molecules, like proteins and RNA, can be transported into cells by the facilitation of ligand transmembrane proteins. For example, the direct active transport with $Na^+/K^+$ ATPase is established by the active transport of both ions. Specifically, cytosol in human cells contains a concentration of potassium ions ($K^+$) that is as much as 20 times higher than in the extracellular fluid, and the extracellular fluid contains a concentration of $Na^+$ as much as 10 times greater than within the cell. By the known sodium potassium pump mechanism, three $Na^+$ ions are actively transported out of the cell for every 2 $K^+$ ions pumped into the cell. This process helps establish a net charge across the plasma membrane with the interior of the cell being negatively charged with respect to the exterior. The resting potential may prepare nerve and muscle cells for the propagation of action potentials leading to nerve impulse and muscle action.

Normally, accumulation of sodium ions outside of the cells draws out the cells ability to maintain osmotic balance, wherein the gradient of sodium ions is harnessed to provide the energy to run several types of indirect pumps. The importance of the roles of $Na^+/K^+$ ATP may be reflected in the fact that almost ⅓ of all energy from mitochondria in human cells is used to pump. In the healing process, the antimicrobial cream of the present disclosure may help human cells regulate osmosis balance by the presence of both Brilliant Blue and sodium laureth sulfate, while also assuring stability by the balance of $Na^+$ ions in fixing the $Ca^{2+}$ ions. $Zn^{2+}$, $Fe^{2+}$, $Fe^{3+}$, and $Al^{3+}$ may act as pumps, attracting $Na^+$ and providing the necessary ions for regeneration of damaged cells to wounds, burns, infections, and the like, while ensuring harmony and normal cellular function.

$Ca^{2+}$/ATPase:

$Ca^{2+}$/ATPase is located in the plasma membrane of all eukaryotic cells, which use the energy provided by one molecule of ATP to pump $Ca^{2+}$ ions in and out of the cell. This activity helps to maintain concentration gradients between the cytosol and outside of the cell. During the process of healing rounds and burns, all elements, vitamins, and minerals, including $Ca^{2+}$ may be beneficial to regenerate cells. In the green antimicrobial cream of the present disclosure, calcium is present, as evidenced by the chemical structure of the final product.

The Role of Silicon Contained in the Green Clay Cream:

Silicon may allow molecular structures to be established and the metabolism to function. Specifically, silicon may be necessary for the synthesis of collagen, elastin, and hyaluronic acid. Thus, silicon may influence the formation of connective tissue, including cartilage, bone, and skin, and may improve a body's immunity. The silicon may initiate the growth and regeneration of cells and body structures. In elastin and collagen, silicon may protect the vascular wall, veins, and arteries. With respect to the skin, the silicon may act as the dermis that the epidermis finds itself attached to.

Silicon may also play a role when it comes to the immune system and hormones. As mentioned above, silicon may be essential for formation of the skin, joints, nails, and hair and, thus, its presence may improve healing, which improves the immune system, maintains flexibility, and strengthens blood vessels. Silicon's presence may also prevent aging and inflammation. Silicon may also help with electrical connections in the brain and other areas of the body. Because silicon is such a prevalent and beneficial element, the green cream clay that contains silicon may help regenerate skin in wounds, burns, and ulcers.

Moreover, silicon is tetravalent, meaning it may be able to create hydrogen bonds with nitrogen and oxygen in wounds, allowing it to react with molecules containing these two elements. The silicon may thus consolidate the structure or promote the enzymatic catalysis of certain molecules, such as collagen, elastin, phospholipids, and structural proteins, such as hyaluronic acid and glucosamine.

The skin cream of the present disclosure may, therefore, comprise an antimicrobial, kaolinite and montmorillonite green cream clay composition with weak acids (fatty acids), oleic acids, benzoic acids, clove oil (C5, C14 antimicrobial properties and anti-aging abilities and properties), trace elements, vitamins, and mineral elements. The final skin cream may provide the ability and function of healing skin disease, Buruli ulcers, wounds, and burns without spots or scars. In some embodiments, the cream may be used with poultice and compresses for burns and deep wounds.

Antimicrobial Abilities of the Cream of the Present Disclosure

The Kaolinite structure unit includes alternating layers of tetrahedral silica with tips embedded in an alumina (gibbsite) octahedral unit. The chemical formula may be $Al_2(Si_2O_5)(OH)_4$. Common mineral elements that may be present include Fe, Mg, Na, K, Ti, Ca, and $H_2O$. The gelatin may contain Zn, Cu, and Ca. The water may contain Mg, Na, Ca, Fe, Zn, Cu, K, and Mn.

As described above, the composition may also include talc ($H_2Mg_2(SiO_3)$ or $Mg_3SiO_{10}(OH)_2$, wherein the talc may include Mg, Mn, Ti, Fe, and Ca and, thus, the talc may be the source of magnesium and silicon. Talc is a mineral that develops during chemical reactions produced by the circulation of hydrothermal fluids rich in silica in magnesium rocks. The minerals most commonly associated with talc are chlorites. Other associated minerals are tremolite, serpentine, snthophyllite, actinote, magnesite, dolomite, and chromite.

Lauryl ether sulfate and Brilliant Blue or Blue Tartrazine may be beneficial in the process of wound healing, and they may have antimicrobial properties. Specifically, these molecules may provide for polystyrene cation exchange. Sodium polystyrene effects the exchange of sodium and potassium in the body. Sodium polystyrene sulfonate may be used to treat high levels of potassium in the blood, also called hyperkalemia. In the cream of the present disclosure, the ions present in the product may exchange the cations necessary for skin regeneration, wound healing, and treating skin infections by creating an antimicrobial compound (zin coceth sulfate, magnesium coceth sulfate) and introducing the ions necessary to reactivate and regenerate damaged cells in the wound or infection.

The presence of lauryl ether sulfate, talc, and gelatin causes the composition to acquire a montmorillonite structure and function, wherein the structure comprises two silica layers and one alumina layer, wherein the alumina octahedral layer is sandwiched between two silica layers with tetrahedral tips. The interlayer bonding between the tops of the silica layers is mainly due to Van der Waals forces and, thus, has the composition may include a high presence of hydrogen or other ion bonding, such as $Na^+$, $Ca^{2+}$, $K^+$, $Mg^{2+}$, $Zn^{2+}$, $Al^{3+}$, $Fe^{2+}$, $Fe^{3+}$, $Cu^+$, $Cu^{2+}$, and $Ti^{4+}$.

Hard metal and heavy metal ions ($Ca^{2+}$, $Zn^{2+}$, $Mg^{2+}$, $Fe^{3+}$, $Fe^{2+}$, $Al^{3+}$, and the like) are contained in the cream of the present disclosure. Sodium ($Na^+$) may be considered a weak or soft metal ion and is contained in the lauryl ether sulfate and Brilliant Blue or Blue Tartrazine. Like polystyrene sulfonate, lauryl ether may exchange its sodium ion and capture a heavy metal contained in the gray clay during the synthesis process, acquiring the antimicrobial properties described above. An exemplary compound that may be formed during the synthesis of the cream of the present disclosure is zinc coceth sulfate, the structure of which is shown below:

Zinc coceth sulfate may be obtained by cation exchange including the migration of a heavy metal into polystyrene sulfonate, wherein the weak ion (sodium in the sodium ether lauryl sulfate) may be displaced by the polystyrene sulfonate and captured by the zinc ions contained in the clay.

Zinc coceth sulfate may be useful for treating skin disorders associated with *Propionibacterium acnes*.

The synthesis of zinc coceth sulfate is shown below:

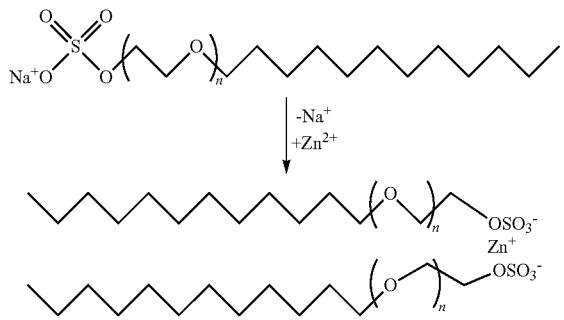

Another exemplary compound that may be formed is magnesium ($Mg^{2+}$) coceth sulfate, the structure of which is shown below:

Magnesium coceth sulfate has antimicrobial properties and may be important in the treatment of skin infections, particularly when a person has a large wound or poor skin restoration abilities due to diabetes, psoriasis, leprosy, and Buruli Ulcers. The magnesium binds calcium and is involved in calcium metabolism on the parathyroid glands. At the cellular level, it controls and regulates the entry of calcium into the cell and intracellular fluids.

Magnesium may inhibit cation channels, such as sodium and calcium receptors, and may act as a calcium antagonist. It may thus protect mitochondria against calcium overload. In the wound healing process, magnesium may play primarily an intracellular role. Also, formed is $MgCl_2$. The $MgCl_2$ present in the composition of the present disclosure may allow damaged cells to regain their phagocytic power in a large proportion.

Polystyrene Exchange Process

The exchange process may be performed by lauryl ether sulfate and brilliant blue, which may act as pump membranes with the ability to displace soft or weak metals by fixing hard metals in the damaged cells, wherein the hard metals may help with cell regeneration. They may also act as a barrier between the heavy metal and the sodium ion by establishing the barrier and controlling the flux of ions (mainly sodium) in the body. The barrier may help to fix ions ($Ca^{2+}$, $Mg^{2+}$, $Mn^{2+}$, $Fe^{2+}$, and $Fe^{3+}$) in the human body with the purpose of wound healing and treating skin infections. Moreover, they may act as a regulator of osmosis activity between extra and intra cells by maintaining flux of important mineral elements through damaged cells (wounds, burns, skin infections, etc.). They may additionally act to rehabilitate skin minerals in the case of alopecia treatment, and to rejuvenate the skin and help prevent or combat wrinkles, and, finally, to prevent sodium ions from penetrating into cells and manage osmotic pressure between the intra and extra cellular environment, balancing the pressure within the cells.

In the composition of the present disclosure, the polystyrene exchanges the heavy metal by displacing $Na^+$, creating more antimicrobial compounds, which may be helpful in healing wounds and skin infections. Many new compounds may be formed by the exchange of sodium ions. The compounds also include calcium coceth sulfate, magnesium coceth sulfate, zinc coceth sulfate, iron coceth sulfate, potassium coceth sulfate, and the like. The structures of these compounds are shown below:

Calcium ($Ca^{2+}$) coceth sulfate:

Magnesium ($Mg^{2+}$) coceth sulfate:

Zinc ($Zn^{2+}$) coceth sulfate:

Iron (ii) ($Fe^{2+}$) coceth sulfate:

Iron (iii) ($Fe^{3+}$) coceth sulfate:

Potassium ($2K^+$) coceth sulfate:

Aluminum ($Al^{3+}$) coceth sulfate:

Manganese ($Mn^{2+}$) coceth sulfate:

Copper (ii) ($Cu^{2+}$) coceth sulfate:

Copper (i) ($Cu^+$) coceth sulfate:

Titanium ($Ti^{4+}$) coceth sulfate:

Molybdenum ($Mo^+$) coceth sulfate:

The exchange processes are outlined below, wherein Brilliant Blue or Blue Tartrazine is the polystyrene sulfonate.

The antimicrobial compound may also include $Ca^{2+}$ ions as a result of calcium chloride. $Ca^{2+}$ intracellular processes may enhance wound healing and skin disease therapy:

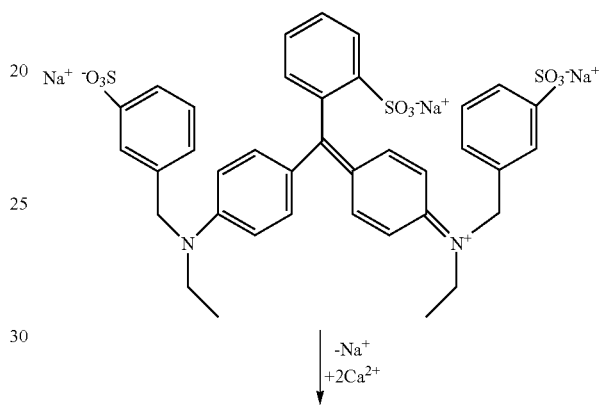

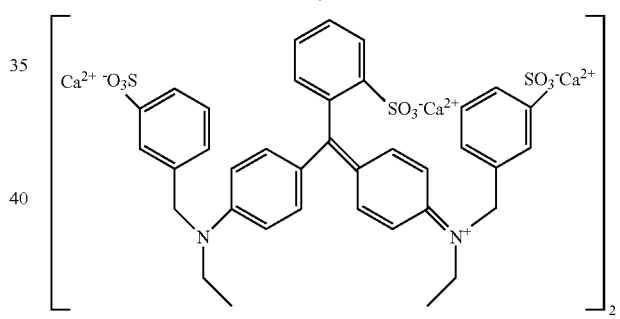

The antimicrobial compound may include magnesium via a reaction with magnesium chloride, wherein $Mg^{2+}$ may improve wound healing and skin disease therapy.

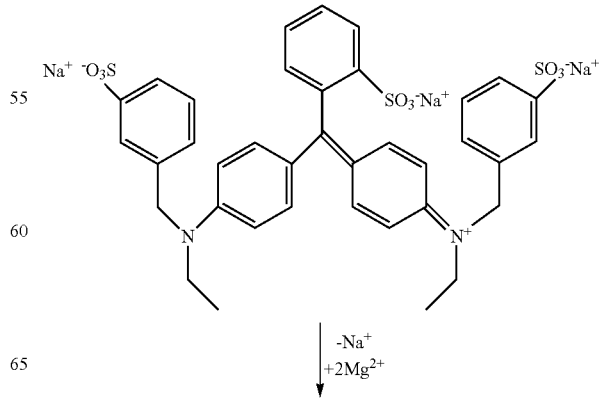

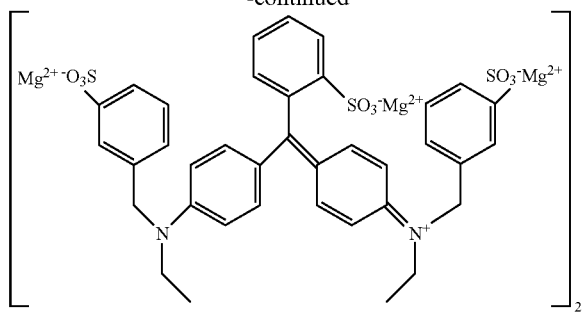

The antimicrobial compound may include zinc ions, wherein $Zn^{2+}$ may improve intracellular processes involved in wound healing and skin disease therapy. In the cream of the present disclosure, zinc plays an important role in the structure of proteins and cell membranes. A finger-like structure, known as a zinc finger motif, stabilizes the proteins. Copper provides the catalytic activity for the antioxidants enzyme, copper zinc superoxide dismutase (CuZn-SOD). Zinc proteins regulate gene expression by acting as transcription factors binding to DNA and influencing the transcription of specific genes.

Zinc also plays a role in cell signaling to influence hormone release and nerve impulse transmission. Zinc plays a role in apoptosis, a critical cellular regulatory process with implication for growing and development. Zinc is also an essential trace mineral for DNA synthesis, cell division, collagen formation, protein synthesis, and immune function, which are all necessary processes for tissue regeneration and wound repair. Zinc is also necessary to develop and activate T-lymphocytes, which are important to the immune system.

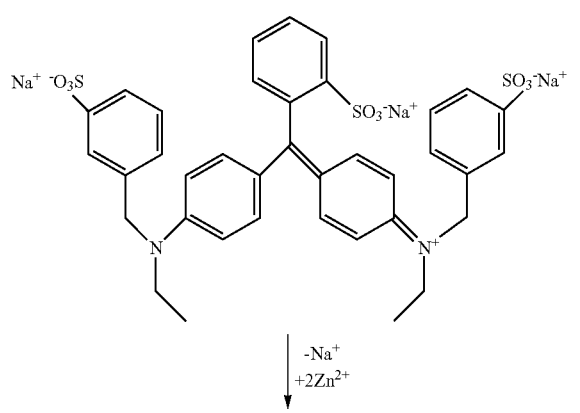

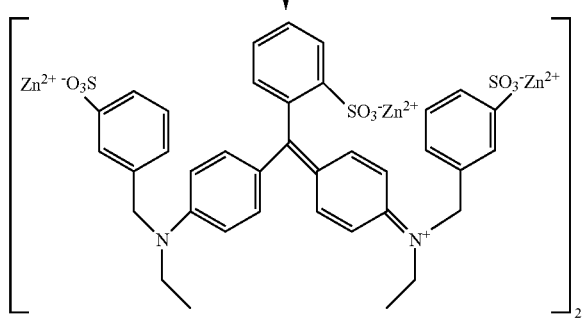

The antimicrobial compound with iron (II) may improve intracellular processes involved in wound healing and skin disease therapy, because iron may play a key role in both oxidative stress and photo-induced skin damage. Iron may be considered a vital co-factor for proteins and enzymes involved in energy metabolism respiration DNA synthesis. Iron may have a specific function, such as the metabolism of collagen by procollagen-proline dioxygenase.

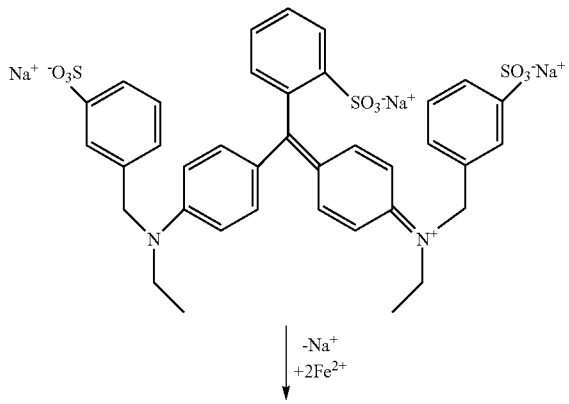

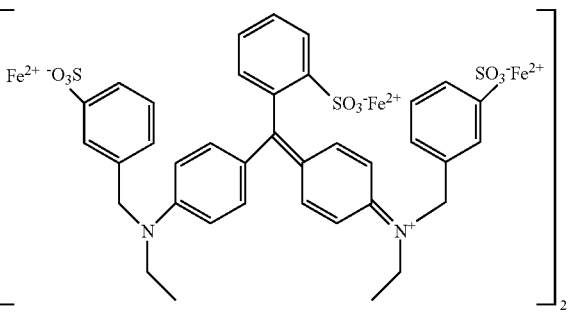

The antimicrobial compound may include iron (III) ions, which may improve intracellular processes involved in wound healing and skin disease therapy, wherein iron is a transition metal that may exist in two stages: $Fe^{2+}$ and $Fe^{3+}$. Intracellular labile may undergo redox cycling between its two most stable oxidations states and react as a superoxide anion with hydrogen peroxide giving hydroxyl radicals. In this process, iron (II) and iron (III) may be used to transport oxygen or catalyze electron transfer reactions, nitrogen fixation, or DNA synthesis.

Four copper containing enzymes, known as multi-copper oxidase (MCO) or ferroxidases, have the capacity to oxidase ferrous iron ($Fe^{2+}$) to ferric iron ($Fe^{3+}$), which is the form of iron that may be loaded onto the protein transferrin for transport to the site of red blood cell formation. The MCO family comprises the circulating cerruplasmin, the membrane bound cerruplasmin, and two proteins. The cuproenzyme, tyrosinase, is required for formation of the pigment melanin, which is formed into cells called melanocytes and plays a role in the pigmentations of hair, skin, and eyes. The cerruplasmin may function as an antioxidant in two different ways. Free copper and iron ions are powerful catalysts of free radical damage. By binding copper, cerruplasmin prevents free copper ions from catalyzing oxidative damage.

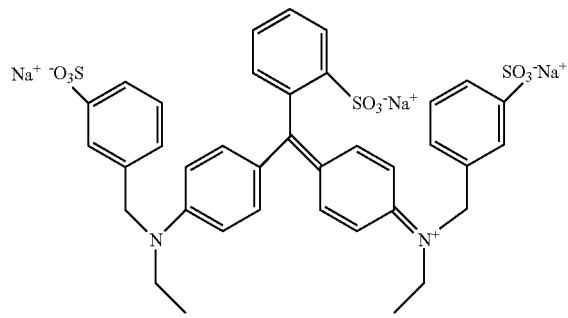

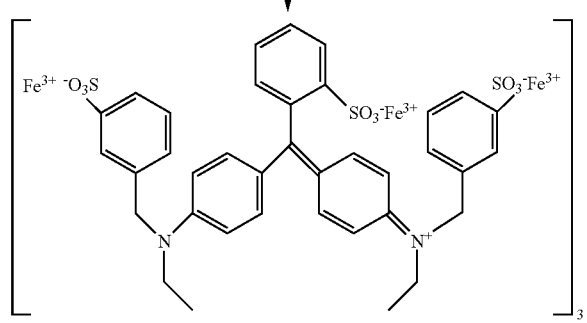

The antimicrobial compound may include potassium ions, wherein $K^+$ may improve intracellular processes involved in wound healing and skin disease therapy. In the present disclosure, the sodium does not penetrate the cells because of two barriers—the heavy metal with the pump polystyrene sulfonate and $Na^+/K^+$ ATP. Actively, there are 3 $Na^+$ transported out of the cell for every 2 $K^+$ pumped into the cell. This process helps establish a net charge across the plasma membrane with the interior being negatively charged with respect to the exterior.

Moreover, potassium is the principal positively charged ion (cation) in the fluid inside the cells, while the sodium is the principal cation in the fluid outside the cells. Potassium concentrations are about 30 times higher inside than outside cells, while sodium concentrations are more than 10 times lower inside than outside cells. The concentration difference between potassium and sodium across the cell membrane may create an electrochemical gradient known as the membrane potential.

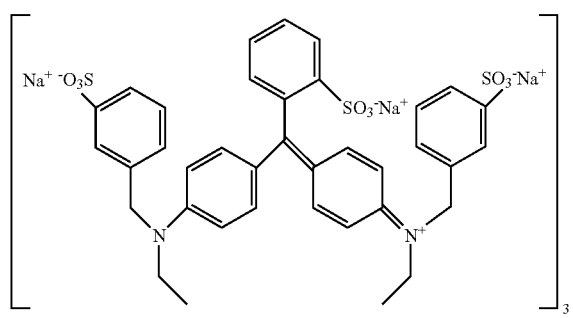

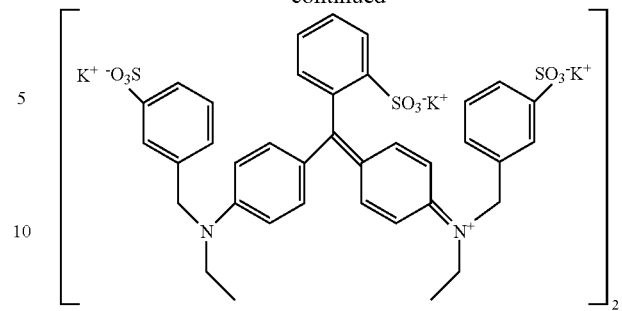

The antimicrobial compound may also include $Al^+$ ions, wherein there may be a correlation between silicon and aluminum ions. Silicon and aluminum $[AlSiO_4]^-$, $(SiO_2)$ may provide stability in a biological environment. Silica may increase the anti-inflammatory capabilities under the control of aluminum. In the wound healing process, silicon may extract abnormal aluminum proteins in damaged cells and, thus, help accelerate skin regeneration. In the composition of the present disclosure, aluminum together with silicon may help initiate and regularize the immune system in wounds, burns, and skin lesions. Silicon may reduce or regulate the multiplication of fibroblasts in the healing process of wounds, burns, lesions, and skin regeneration.

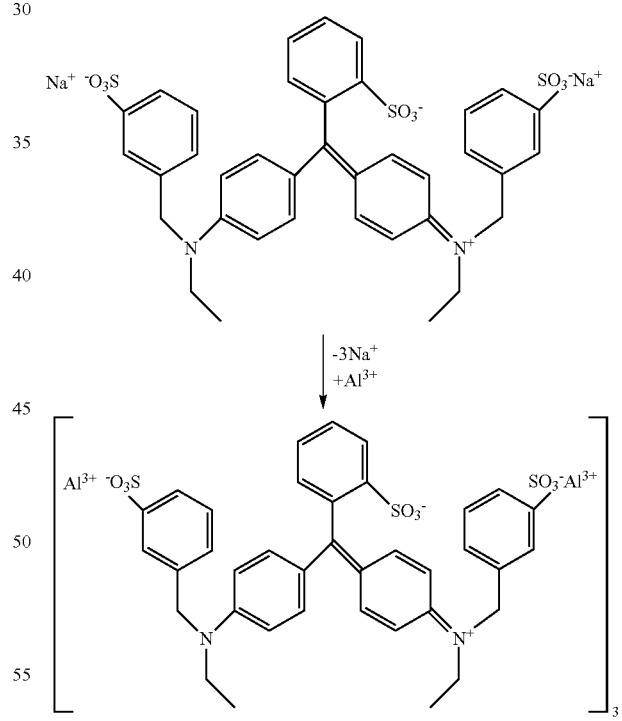

The antimicrobial compound may also include $Cu^{2+}$ ions, wherein the intracellular processes may enhance wound healing and skin disease therapy. Copper plays a key role in angiogenesis and in the expression and stabilization of extracellular skin proteins. Copper may also be an essential cofactor for oxidation-reduction reactions involving copper containing oxidases. Copper enzymes regulate various physiologic pathways, such as energy production, iron metabolism, connective tissue maturation, and neurotransmission. Thus, copper may be considered an essential trace element for humans and animals. In the body, copper shifts between the cuprous ($Cu^{2+}$) and cupric ($Cu^+$) forms; although, the majority of the body's copper is in the cuprous form.

The copper dependent enzyme, cytochrome c oxidase, plays an important role in cellular energy production. By catalyzing the reduction of molecular oxygen to water, cytochrome c oxidase creates an electrical gradient used by the mitochondria to create ATP. Another cuproenzyme, lysil oxidase, is required for the cross-linking of collagen and elastin, which may be important for the formation of strong and flexible connective tissues, which helps maintain the integrity of connective tissue in the heart and also plays a role in bone formation.

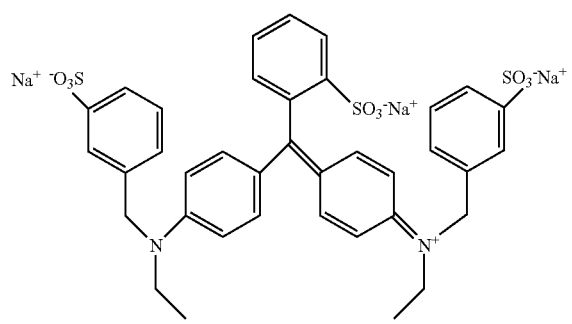

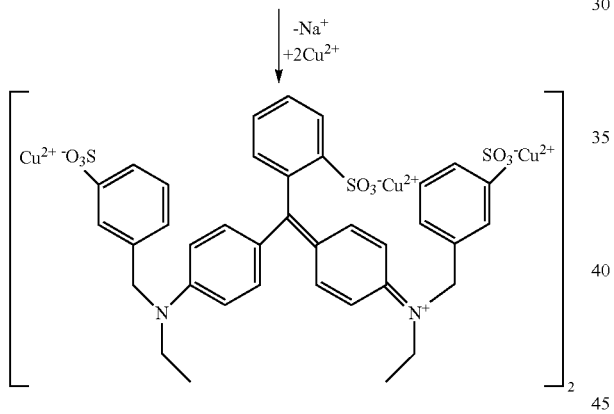

The antimicrobial compound may also include $Cu^+$ ions, wherein the intracellular processes may enhance wound healing and skin disease therapy:

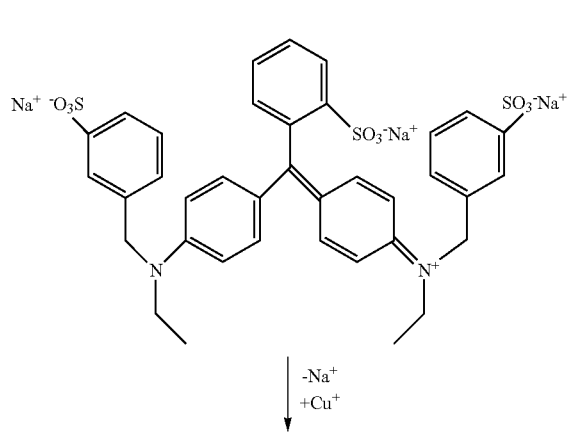

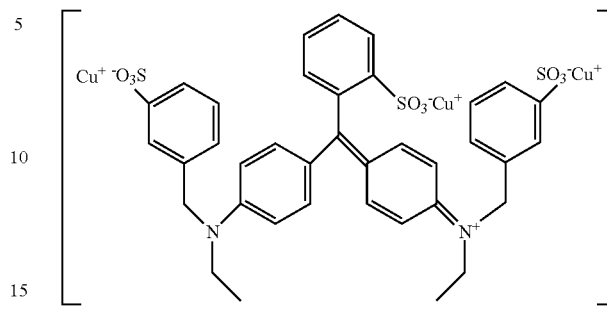

The antimicrobial compound may also include $Mn^{2+}$ ions, wherein the intracellular processes may enhance wound healing and skin disease therapy. Wound healing is a complex process that requires increased production of collagen. The manganese in the cream of the present disclosure may activate prolidase, which is an enzyme that functions to provide the amino acid, proline, for collagen formation in human skin cells. Glycosaminoglycan synthesis, which requires manganese-activated glycosyltransferases, may also be important in wound healing.

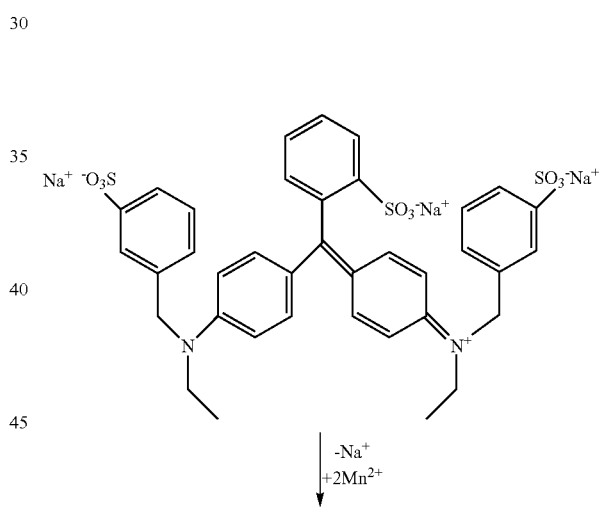

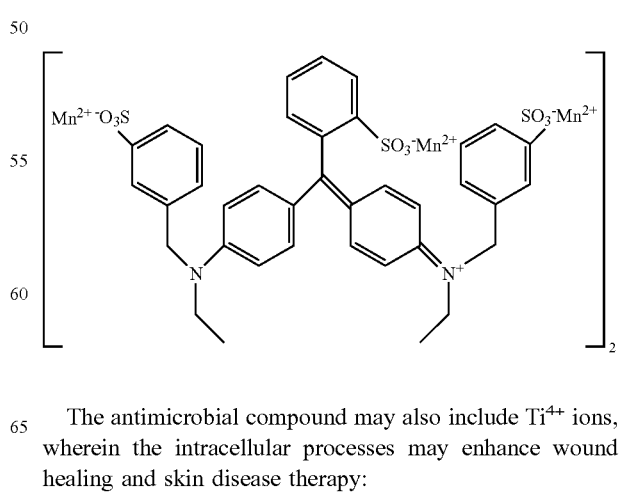

The antimicrobial compound may also include $Ti^{4+}$ ions, wherein the intracellular processes may enhance wound healing and skin disease therapy:

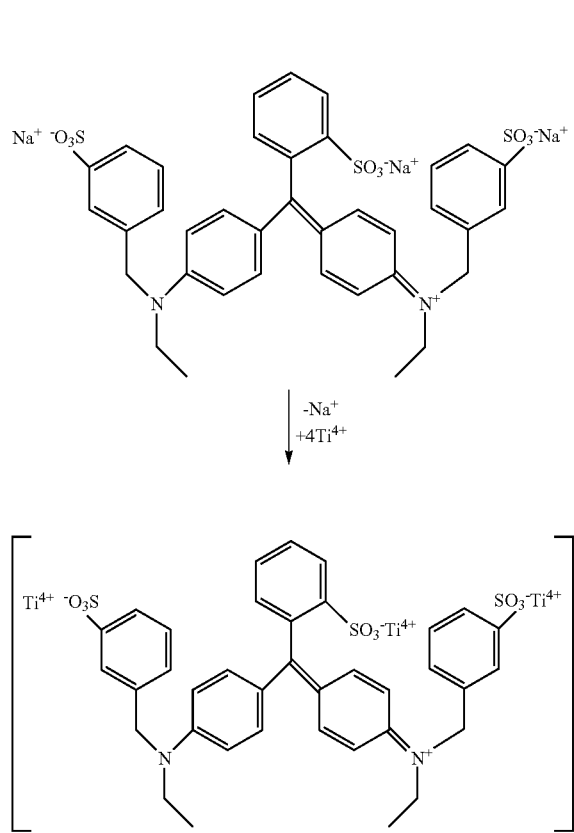

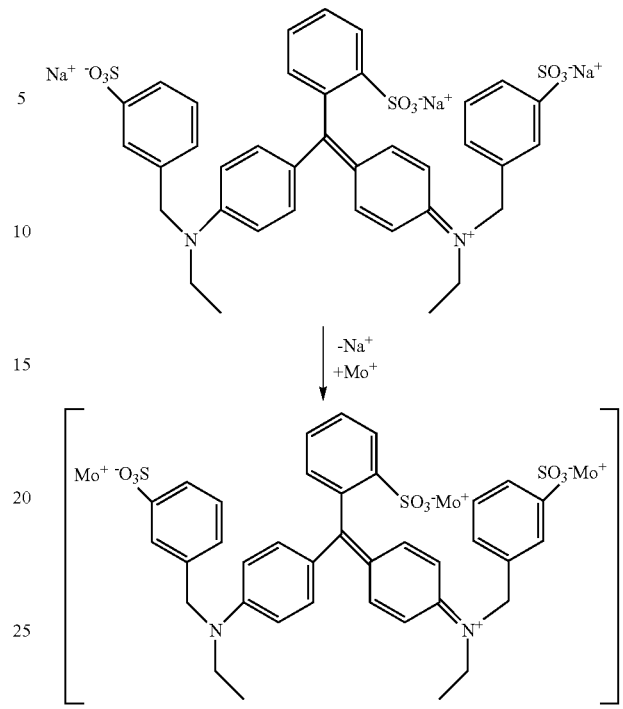

The antimicrobial compound may also include $Mo^+$ ions, wherein the intracellular processes may enhance wound healing and skin disease therapy. Molybdenum is a trace element that may be beneficial in the activation of various chemical reactions and to eliminate certain products synthesized during the digestion of the proteins. It also participates in the metabolism of fatty substances. Molybdenum may be essential for the metabolism of taurine, and it may intervene in the metabolism of sulfur and in the needs to copper. Molybdenum is an antagonist of copper. In the case of a molybdenum deficiency, there may be an intolerance to sulfur amino acids: cysteine and methionine. A deficiency in molybdenum may hinder the metabolism of the nitrogen from which a possible chlorosis forms (a form of anemia with the greenish huge of the skin). Molybdenum may catalyze xanthine oxidase to bind iron to ferritin. Antianemia may be a vital property of the enzyme responsible for the use of iron. It promotes the intestinal absorption of the iron as well as its destocking within the organism. Specifically, ferroxidase activity of ceruloplasmin may facilitate iron binding into its transport protein, transferrin, and may prevent free ferrous ions from participating in harmful free radical generating reactions. The regulation of gene expression cellular copper levels may affect the synthesis of protein by enhancing or inhibiting the transcripts of specific genes. Copper may regulate the expressions by increasing the level of intracellular oxidative stress. Finally, adequate copper amounts in the body may be necessary for normal iron metabolism and blood cell formation.

When it comes to magnesium coceth sulfate, magnesium chloride may activate the phagocytic leukocyte. Thus, magnesium chloride in the cream of the present disclosure may allow damaged cells to regain their phagocytic power in a proportion of about 300%. Thus, the magnesium chloride may help with the wound healing process.

The human body requires essential heavy metals, include Cu, Zn, Mg, and Ca, to carry out biological functions. In the biological system, the metals are mostly bound to proteins. The metalloproteins have both catalytic and structural roles, such as the following: (i) as a constituent of enzyme active sites; (ii) for stabilizing enzyme tertiary or quaternary structure; (iii) for forming weak bonds with substrates, contributing to their orientation to support chemical reactions; and (iv) for stabilizing charged transition sites. Cu, Fe, and Mn have an impaired (or unpaired) electron that allows for their participation in redox reactions, such as those at enzyme active sites.

Mn has unpaired electrons that allow for its participation in redox reactions at enzyme active sites. Cu mediates the reduction of one superoxide anion to hydrogen peroxide and oxidation of a second superoxide anion to molecular oxygen in the active site of cytoplasmic superoxide mutations. Zn has no unpaired electrons in $Zn^{2+}$ and it may prevent the formation of harmful free radicals by competing with the redox active metals, such as Fe and Cu, at the enzyme active sites. The heavy metals may be immediately complexed with molecules or peptides upon entry to the cell.

Biological Function of Lauryl Ether Sulfate and Brilliant Blue:

In the antimicrobial composition of the present disclosure, the presence of sodium laureth sulfate and brilliant blue or blue tartrazine react like a pump membrane and as a barrier between heavy metals and sodium ions by establishing barrier and control the flux of ions in the human body, mainly the sodium ion. This barrier may help fix ions in the human body for wound healing and treating skin infections. It may also react as a regulator of osmosis activity between intra and extracellular by maintaining flux of important elements through damaged cells in skin regeneration and the treatment of skin diseases. It may also rehabilitate mineral elements of the skin in the case of, for example, alopecia treatment. It may also rejuvenate skin and help prevent wrinkles and help the skin remineralize. Lastly, it may penetrate into cells and manage the osmotic pressure for the balance of pressure within cells.

Biological Function of Sodium Chloride or Sodium Ions:

Sodium does not penetrate the cells because of the barrier created by the heavy metal. Thus, the sodium in the composition of the present disclosure does not penetrate the protective membrane. As a result, a net charge is established across the plasma membrane with the interior being negatively charged with respect to the exterior. The accumulation of salt outside of the cells may help maintain osmotic balance of the sodium gradient. The osmotic balance may be fixed by the polystyrene membrane by fixing heavy metal ions into the cells and displacing sodium ions. Finally, sodium ions do not have any biologic function in the wound healing process and skin disease treatment. Rather, the sodium chloride may soften the bond in the composition of the present disclosure. The salt in the cream of the present disclosure may have a cosmetic functions, helping to effectively clean the skin.

Certain molecules and salts included in the composition of the present disclosure may promote the healing of wounds and burns without spots and scars. Those salts include, for example, acidified sodium chloride (NaCl→Na$^+$, Cl$^-$), zinc coceth sulfate, magnesium coceth sulfate, potassium coceth sulfate, calcium coceth sulfate, aluminum coceth sulfate, and aluminum chloride (Al$^{3+}$, Cl$^-$→AlCl$_3$).

Correlation between Silicon and Aluminum: In the composition of the present disclosure, there may be a correlation between silicon and aluminum reactivity. The correlation demonstrates the link of both elements. Thus, silicon prefers coordination numbers with a tetrahedral atomic environment, while aluminum prefers octahedral coordination in hydrated cations, oxides, hydroxides, and coordination complexes. The isoelectric relationship between $(SiO_2)_2$ and $[AlSiO_4]^-$ may be the foundation of vast aluminosilicate chemistry.

In the case of a clay mineral, this correlation may be:

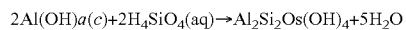
$$2Al(OH)a(c)+2H_4SiO_4(aq) \rightarrow Al_2Si_2Os(OH)_4+5H_2O$$

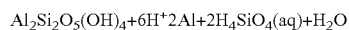
$$Al_2Si_2O_5(OH)_4+6H^+2Al+2H_4SiO_4(aq)+H_2O$$

The presence of Al$^{3+}$ may react with Cl$^-$ to create aluminum chloride to stimulate skin regeneration and wound healing.

Potassium Reactivity:

The potassium content in the composition of the present disclosure may be provided by two sources, the water and the kaolin composition. In the kaolin, the K$^+$ ions may be removed by hydrolysis of the kaolin. During its formation, hydrolysis occurs, causing H$^+$ or OH$^-$ to replace ions in the mineral, as explained by the following reaction:

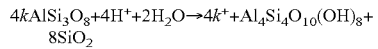
$$4kAlSi_3O_8+4H^++2H_2O \rightarrow 4k^++Al_4Si_4O_{10}(OH)_8+8SiO_2$$

Thus, K$^+$ is removed by dissolution into water. Therefore, in the composition of the present disclosure, the k$^+$ may be activated by processing a mechanical energy in the presence of lauryl ether sulfate and brilliant blue, causing the K$^+$ ion to integrate the interlayer position. Additionally, the mechanical energy may allow the oxygen to react with the composition in the presence of water and lauryl ether sulfate. Thus, the follow complete dissolution may be activated by the mechanical energy:

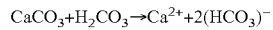
$$CaCO_3+H_2CO_3 \rightarrow Ca^{2+}+2(HCO_3)^-$$

Wherein K$^+$ is integrated in the interlayer position activated by the mechanical energy during the synthesis process.

Metal and Metalloprotein Sources of the Antimicrobial Cream

In the composition of the present disclosure, the phyllosilicates may be based on a framework of 02 and OH$^-$ ions, which may occupy the summits of octahedral assemblies. Cations of various sizes, such as Si$^{4+}$, Al$^{3+}$, Fe$^{3+}$, Fe$^{2+}$, Mg$^{2+}$, Ti$^{4+}$, Cu$^{2+}$, Cu$^+$, Mn$^{2+}$, and Mo$^+$, may be positioned within the elementary structural cavities. This ions are also called metalloproteins, which may have four sources: (1) water; (2) kaolin mineral, (3) talc ($H_2Mg_3(SiO_3)$) or $Mg_3SiO_{10}(OH)_2$; and (4) gelatin. The final product may be $(Al,Zn,Fe^{3+},Fe^{2+},MgO,Mn,Cu^{2+},Cu^+,Ti,Mo^+)$ $Si_4O_{10}(OH)_2$ K$^+$Na$^+$Ca$^{2+}$.

(1) Water: in the composition of the present disclosure, water reactivity may be very important. Water has strong hydrogen bonds, and at room temperature, pure water should be solid. However, the presence of the hydrogen bonds linking the molecules together gives the molecules very particular characteristics and structuring. The structuring is due to the formation of oriented hydrogen bonds, which associate the molecules into tetrahedral structural units and, thus, the liquid differs totally from a stack of molecules that tends to be as dense as possible. The predominant Van der Waals interaction is the interaction of keesom (69%) (dipole-dipole interaction), then the interaction of London (polarization interaction), which is created by the charges induced by the external polarization field. With the presence of lauryl ether sulfate, the molecules subjected to the dipolar interactions may be the predominant interactions in liquid water, and these interactions may be modified in the composition of the present disclosure by the distribution of charges and their way of reacting to the external field. In the clay structure, water molecules modify the cation-clay surface interactions by creating interactions between cation or charged surface and water molecules. This reorganization of the network of interactions existing in the clay structure affects the ability of the clays to hydrate. Water molecules, lauryl ether sulfate, and fatty acids will swell the clay structure and strengthen cation-surface interaction. This implies two things: (1) during hydration, the charges present in the clay structure change as the amount of water increases, and (2) the variation in partial loads depends on the compensating cation and its hydration energy. The modifications of the loads may allow the clay to absorb more water, facilitating the spacing of the antimicrobial cream's layers. This dynamic aspect of the electrical interactions may help the composition create the biological environment to process the remineralization of the skin and healing wounds by the hydration of clays, which may be the cause of the swelling of mineral clays. In the vicinity of the interface with clay, the water may have its structure modified by interactions by the surface.

The water's composition may include calcium ions 112 mg/L; magnesium ions 12.5 mg/L; silicon dioxide 7.1 mg/L; potassium ions 2.5 mg/L; sodium ions 10 mg/L; zinc ions 3.5 mg/L; copper 1.1 mg/L; iron 0.3 mg/L; and manganese ions 0.05 mg/L.

(2) Kaolin mineral (clay mineral composition): in the composition, the clay mineral may absorb certain ions and retain them in an exchangeable state, wherein exchangeable ions are held on the external surface of the mineral, and the exchangeable ions do not affect the structure. The following list presents the most exchangeable cations in order of usual relative abundance: $Ca^{2+}$, $Mg^{2+}$, $H^+$, $Na^+$, $Fe^{3+}$, $Fe^{2+}$, $Ti^{4+}$, $Cu^{2+}$, $Cu^+$, $Mn^{2+}$, and $Mo^+$.

The clay (kaolin) composition may have a pH of about 7.3 and may comprise the following: $SiO_2$ (48.10%); $Al_2O_3$ (36.85%); $Fe_2O_3$(0.05%); $TiO_2$ (0.52%), $CaO$ (0.28%); and $K_2O$ (0.36%), wherein all percentages are mass percentages.

(3) Talc ($H_2Mg_3(SiO_3)$ or $Mg_3SiO_{10}(OH)_2$): talc is a hydrous magnesium silicate mineral. Although the composition of talc usually stays close to the above generalized formula, some substitution does occur. Small amounts of Al or Ti can be substituted for Si; small amounts of Fe, Mn, and Al can be substituted for Mg; and very small amounts of Ca can be substituted for Mg. When large amounts of Fe substitute for Mg, the mineral is known as minnesotaite. When large amounts of Al is substituted for Mg, the mineral is known as pyrophyllite.

The talc composition may include the following: magnesium (19.23% Mg and 31.88% MgO); silicon (29.62% Si and 63.37% $SiO_2$); hydrogen (0.53% H and 4.75% $H_2O$); and oxygen (50.62% 0), wherein all percentages are mass percentages.

(4) Gelatin: as a denatures product of collagen, gelatin contains may divalent metal ions, such as calcium, copper, and zinc that can form ionic bonds with carboxylic acid and groups on the gelatin polypeptides, influencing the organization for the gelatin network. However, there is little information on the impact of divalent ions on the stability and mechanical properties of gelatin hydrogels. Removal of the metal ions may free the carboxylic acid group in polypeptide molecules, thereby strengthening the electrostatic interactions between the carboxylic acid groups and also improving the crosslinking density upon chemical crosslinking, eventually improving the mechanical strength and stability in the antimicrobial composition. The gelatin may provide stability, strengthen the link by influencing the electrostatic relations between lauryl ether sulfate, Brilliant Blue, metalloproteins, and the tetrahedral and octahedral relationships of aluminum (gibbsite) and silicate ($SiO_2$).

Cation Exchange Acceleration:

there may be two major reasons for cation exchange acceleration in the composition of the present disclosure. (1) The amount of sodium chloride and the polystyrene sulfonate (Brilliant Blue and lauryl ether sulfate) may accelerate the exchange because of polystyrene sulfonate's properties. They may each also act as a softening agent due to Van der Waals forces between the top silica layers. (2) The broken bonds around the crystal edge and the substitution within the lattice and the hydroxyl hydrogen surface may be exchangeable, because the $OH^-$ concentration increases the negative charges at the edges according to, for example, the following: $SiOH+OH^- \rightarrow SiO^- + H_2O$. The same applies to Al—OH at the exposed base surface.

Properties and Characteristics

The green tea in the cream of the present disclosure may help fight inflammation. Moreover, the green tea has antioxidant properties and may enhance the wound healing process. The salt may have strong cleansing properties. The talc may be a mineral comprising Mg, Mn, Ti, Fe, and Ca, such as hydrated magnesium silicate ($H_2Mg_3(SiO_3)$ or $Mg_3SiO_{10}(OH)_2$. The menthol ($C_{10}H_{19}OH$) may relieve minor aches and pains. Clove oil may be used for its antiseptic properties. Additionally, it contains eugenol, which has anti-bacterial properties; thus, the clove oil may help clear cystic acne and kill infections, thus reducing swelling. Olive oil may help fight signs of aging. The honey used in the cream of the present disclosure may be a saturated or super saturated solution of sugars. The honey may be diluted by wound exudates, creating hydrogen peroxide via a glucose oxidase enzyme reaction and resulting in antibacterial activity that does not damage the tissue.

The vitamins included in the cream may have various purposes. For example, vitamin A may help rebuild tissue by playing a role in the development of lymphocytes, which are cells that fight off bacteria and disease. Vitamin D may contain effective antioxidants that help fight free radicals in the body. Vitamin C may provide potent antioxidant protection, healing the skin from damage from free radicals, may boost healthy collagen production, may reduce the appearance of brown spots and other sun damage, may reduce inflammation and irritation, may fade post-breakout red marks, and may increase the effectiveness of sunscreens. Vitamins B2 may promote metabolism and mobilize iron from storage to incorporate into cells. Vitamin B6 may help utilize the energy contained in food and is important for carbohydrate, protein, and fat metabolism.

The cream of the present disclosure may have a clay-like consistency, wherein the ingredients of the cream may stimulate the regeneration of skin cells. Thus, facials masks and exfoliating scrubs made with the cream may result in the stem cells located within the skin actively generate differentiating cells that may ultimately form either the body surface or the hairs that emanate from it. The stem cells may be able to replenish themselves, continually rejuvenating the skin and hair.

Plasticity and Breaking Point:

In the antimicrobial cream of the present disclosure, the mechanical properties, such as plasticity and breaking point, may be influenced by the nature and quantity of the absorptive ions, in particular the $Ca^{2+}$ or $Na^+$ ions. The addition of an additional quantity of sodium chloride during the synthesis process may activate the exchange capacity between the clay and the polystyrene sulfonate, namely the Brilliant Blue and the lauryl ether sulfate. However, the ionic strength may not have a considerable effect, so there may be an effect of the loss of surfactant by the precipitation due to the exchange of salts. The absorptions of the anionic surfactant, lauryl ether sulfate, may increase as the concentration of electrolytes or cations increase. The colloids may be provided with negative charge.

Mixed layer clays may comprise a clay that changes from one type to another through a stacking sequence. The cream of the present disclosure is layered in the following order mineralized water (Mg, Na, Ca, Fe, Zn, Mn, K, etc.), fatty acids, lauryl ether sulfate, talc ($Mg_3SiO_{10}(OH)_2$), and mineral kaolin clay contents (60% silica, 26% aluminum, and 14% Mg, Fe, Na, K, Ca, Mo, Ti, $H_2O$), wherein all percentages are mass percentages.

During the synthesis process, the main agent responsible for the chemical reaction together with mechanical energy is water. Because of the presence of (Ca, Na, H)(Al,Mg,Fe, $Zn)_2(si,Al)(O)*H_2O$ and because the most common weak acid that forms in surface water is carbonic acid, the result is $H_2O+CO_2 \rightarrow H_2CO_3+H^+ + HCO_3^-$, wherein the $H^+$ is a small ion that can enter the crystalline structure easily and release another ion. Therefore, with the presence of Brilliant Blue and lauryl ether sulfate together with mechanical energy, the following is formed: $(Al,Zn,Fe,67MgO_{33})Si_4O_{10}(OH)_2Na^+Ca^{2+}$.

Potential Energy and Stereochemistry:

The potential energy provided by the chemical reactions may spin compound movements and provide an extraordinary healing power.

Mutation or Isomorphism and Polymorphism Substitution Structure of Antimicrobial Cream:

The swelling properties of the cream of the present disclosure may be due to the positive interlayer in excess with some OH. The metal oxide and metal may perform isomorphism substitution, wherein they relocate in octahedral and tetrahedral layers. During the synthesis process, there may be two basic components to the structure of a layer of corner linked tetrahedral and a layer of edge sharing octahedral. Because the dominant ions in the cream are $Al^{3+}$ and $Si^{4+}$, they relocate and substitute and produce the deficiency charge that must be balanced. Consequently, isomorphism substitution occurs. Moreover, during the synthesis process, which requires mechanical energy, such as cracking and mixing of kaolin with water, fatty acids, lauryl ether sulfate, and talc, there is about 60 to about 65% by mass silicon. The silicon may be present as montmorillonite (Si—Al—Si) or kaolinite (Al—Si—Al). Magnesium may also be present as montmorillonite (Al—Mg—Al). The alternating $Al^{3+}$ and $Si^{4+}$ layers create a polymorphism substitution, changing the structure and disrupting the crystallinity through kaolinite, chlorite, and montmorillonite. This generally occurs when a chemical compound may crystallize in more than one structure. This change creates the deficiency in charge that needs to be balanced. Thus, the swelling of the composition is caused by two things (1) the isomorphism substitution with compensatory cation imbalance; and (2) the polymorphism substitution activated by the addition of talc, cracking the phyllosilicate clay and polystyrene sulfonate.

The dominant atom in the tetrahedron is the $Si^{4+}$ cation, but the $Al^{3+}$ cation can also be positioned at this site. However, the substitution of the $Al^{3+}$ for $Si^{4+}$ produces a charge deficiency that must be balanced.

The octahedral layers are edge sharing octahedral layers. The phyllosilicate have hydroxyl ($OH^-$) ions involved in the linkage to form layers, in addition to the oxygen.

During the synthesis, the composition of the present disclosure starts with a kaolinite structure with an alternating structure of alumina and silica layers. Once talc is added, the structure changes to montmorillonite with very weak silicate-silicate bonds softened by water, cations ($Ca^{2+}$, $Mg^{2+}$, $H^+$, $Na^+$, $Fe^{3+}$, $Fe^{2+}$, $Ti^{4+}$, $Cu^{2+}$, $Cu^+$, $Mn^{2+}$, and $Mo^+$), lauryl ether sulfate, and fatty acid. The change in structure is due to the large amount of silicon (67% by mass) provided by the talc and kaolinite mineral in the octahedral site, wherein the mixture may also be activated using mechanical energy, which allows some oxygen or $OH^-$ bonds between aluminum and silicon to be broken. There is also the presence of aluminum-silicon bonds and magnesium in the octahedral sites. Due to the structure, the clay may absorb the water between its layers.

Because of the thin layers, the clay gives the water an enormous surface on which chemical reactions may also take place, wherein elements such as potassium, sodium, or calcium may bind to the clay and be given back to the water, each time in exchange with another element from that group. Thus, it may be said that the clay has the ability of "cation exchangers." During this exchange, the macroscopic characteristics of the clay may also change permanently, wherein the clay becomes rough or more plastic and swells. This change may be due to the mixture of kaolin and talc mineral together with the mechanical energy activation. Thus, the presence of talc may cause the change of structure activated by mechanical energy, water, lauryl ether sulfate, and fatty acid.

The composition of the present disclosure is mainly a montmorillonite structure and some kaolinite and chlorite structure. Specifically, each silicate crystal includes a quasi-regular tetrahedral ($(Si,Al)O_4$) whose centers are occupied by silicon or aluminum ions, and the vertices have oxygen ions. The $Si^{4+}$ ion has a radius of 0.039 nm with a coordination number of 4, meaning that it is surrounded by four oxygen atoms, forming a quasi-regular $SiO_4$ tetrahedron. Each of the oxygens is attracted by the central silicon with a stronger binding strength than those of the other cations with which it is also in contact. The aluminum has a radius of 0.057 nm and a coordination number that varies from 4 to 6. The aluminum can thus create $AlO_4$ tetrahedra or $AlO_6$ octahedrons. The tetrahedral $(Si, Al)O_4$ may be independent or may associate by their vertices, but such tetrahedral may not have an edge or face in common. This arrangement of tetrahedral $(Si, Al)O_4$ has a negative charge that neutralizes the cations. The cations, such as hexagonal Mg, Fe, and Al, are found at the centers of the quasi-regular octahedrons of oxygen atoms, the edges of which have a length close to that of the tetrahedron $SiO_4$. Thus, the silicates that have a geochemical significance appear as arrangements of oxygen tetrahedral and octahedral with common edges. The silicates themselves have quasi-regular tetrahedral of the oxygen ions with their centers either including a silicon or aluminum ion, associated by the four vertices to form a three-dimensional framework of $(Si, Al)O_2$ constituting a macroanion whose negative charge is neutralized by certain cations. Because the aluminum atom plays the geometric role of the silicon atom, the silicates appear as aluminosilicates, in which the Si atoms are at least as numerous as the Al atoms. Thus, an oxygen ion may be bonded to two other ions, which makes it inactive or with two ions, $Si^{4+}$ and $Al^{3+}$, giving it an electrostatic valent of 1+¾. This active oxygen is therefore bound to cations from which it receives ¼ of electrostatic valence to neutralize its charge.

Ions, such as $Mg^{2+}$ and $Fe^{2+}$ with a coordination number of 6 at the regular octahedron centers of oxygen atoms have an electrostatic valence of ⅓, which is too large compared to other cations attached to the negative colloids to create an electrostatic bond. Thus, they never enter the chemical composition of silicates. On the other hand, larger ions, such as $Ca^{2+}$ and $Ba^{2+}$ with a coordination number of 8, or alkaline ions $K^+$, $Na^+$, and $Li^+$, whose electrostatic valence remains less than ¼, are suitable. However, in some silicates, small amounts of iron are present in the form of $Fe^{3+}$, which replace $Al^{3+}$ in the oxygen tetrahedral.

In the antimicrobial cream of the present disclosure, the elementary layer may be an octahedral or tetrahedral layer. To form a polymer cream, the octahedral and tetrahedral layers may alternate tetrahedral layers including an octahedral layer, which may cause the isomorphism substitution, polymorphism substitution, and swelling in the cream, which is hydrophilic. The elementary layer bay be succeeded by a complete layer of brucite type $Mg(OH)_2$, in which a part of $Mg^{2+}$ is replaced by $Al^{3+}$. Additionally, in the crystalline forms of the antimicrobial composition, every four points (oxygen atoms) of the $SiO_4$ structure are shared with other tetrahedrals via Van der Waal bonds. The resulting relative amounts of silicon and oxygen in the crystal structure result in the net chemical formula $SiO_2$.

Along with the Van der Waal bonds between the top silicate tetrahedral position, there may also be hydrogen bonds between inorganic colloids, cations, and silicon. This hydrogen bond may influence the silicate to react with the colloid and attach a metal by a weak bond. Because of the structure of the quasi-regular $SiO_4$ tetrahedron wherein the oxygens are attracted to the central silicon with a stronger binding strength than those of other cations, the crystalline structure results in the chemical formula $SiO_2$. Thus, some hydrous metal silicate compounds may be established, and the silicate structure may by hydrous sodium silicate, hydrous potassium silicate, or lithium silicate. These compounds may influence the arrangement of silicate in the composition. These arrangements may be present due to the addition of talc with the kaolin clay mineral and the cracking process during synthesis. Specifically, in the cream of the present disclosure, silicon may be present in certain parts of the cream as follows.

First, silicon may be present in independent silicates, wherein no oxygen atom is bonded to two silicon atoms. The $SiO_4$ tetrahedral anions are associated with cations like $Mg_2SiO_4$, where a hydrogen bond is present between ions and a Van der Waals bond is present at the top of each silicate.

Second, silicon may be present in silicates with finite tetrahedral groups, wherein the tetrahedral of the same group may be combined in the minerals such that an oxygen atom is a common sum with two $Si_2O_7$. Thus, there may be a hydrogen bon between a cation and inorganic colloid and a Van der Waals bond at the top of each silicate, wherein the top of the silicate is defined as the interlayer connection by Van der Waals attractions.

Third, the silicon may be present in silicates arranged in chains, wherein the tetrahedrals combine to form an infinite linear chain, and the corresponding silicates may have a fibrous texture. When the chain is a simple chain, its chemical composition is $SiO_3$, and the properties are similar to the tetrahedral anion $SiO_2(OH)$. This arrangement may include hydrous sodium silicate with a hydrogen bond between colloids and a Van der Waals bond at the top of each silicate.

Fourth, the silicon may be present in a lamellar silicate, wherein the tetrahedron chains pool some of the vertices to form planar networks. Thus, two chains of juxtaposed pyroxenes, of link $SiO_3$, provide the double chain of the amphiboles $Si_4O_{11}$. If the chain continues so that three atoms of each of the tetrahedral are common to three other tetrahedral, a planar array of tetrahedrons bound by three of their vertices whose chemical composition is $Si_2O_5$ is formed.

All of the above structural type of silicates may be rotated and organized during the synthesis process of the cream of the present disclosure due to the swelling process caused by the cation imbalance created with the presence of Brilliant Blue, fatty acids, and lauryl ether sulfate. The structures and ions present in the cream composition provide the cream with properties and qualities that result in extraordinary healing powers. In the presence of gelatin, vitamins, polystyrene sulfonate, and fatty acids, the cream of the present disclosure may have the final chemical formula of:

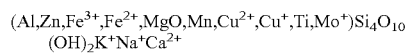

The cream of the present disclosure may help skin respond to two major threats: the loss of blood and the loss of a physical barrier (the epidermis) between patient innards and the outer world. An open cut is an open doorway to bacteria and other pathogens, far more vulnerable to infection. As a result of certain molecules and salts, the cream of the present disclosure may help promote the wound healing process without spots and scarring. Examples of those molecules and sales include acidified sodium chloride, zinc coceth sulfate, magnesium cocet sulfate, silicon, zinc oxide, titanium oxide, titanium coceth sulfate, calcium coceth sulfate, copper coceth sulfate, iron(iii) and iron (ii) coceth sulfate, aluminum coceth sulfate, manganese coceth sulfate, and molybdenum coceth sulfate.

The addition of NaCl to the cream of the present disclosure may accelerate the cation exchange between negative colloids, water, clay, Brilliant Blue, and lauryl ether sulfate. The NaCl stabilizes the pH of the cream of the present disclosure. During the synthesis process, the addition of NaCl may accelerate the cation exchange between negative inorganic colloids and cations container in the water, such as mineral cations provided by talc and kaolin and/or cations provided by lauryl ether sulfate and blue tartrazine. Moreover, the sodium softens the bond in the interlayer, octahedral, and tetrahedral sites. Additionally, the NaCl forms oppositely charged ions that are held together by an ionic bond, forming a crystal lattice. Ionic compounds (KCl, $AlCl_3$, $CaCO_3$, $MgCl_2$, $FeCl_3$, and $Al(OH)_3$) are formed. The reactions are summarized below.

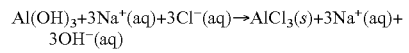

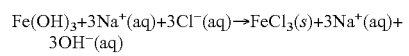

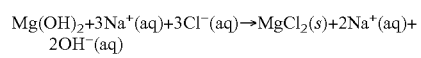

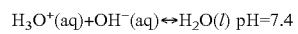

Function of Calcium Carbonate Hydrolysis in the Antimicrobial Cream:

In the cream of the present disclosure, the buffer system ($H_2CO_3/HCO_3^-$) stabilizes the pH to 7.4. With the presence of water, the following occurs:

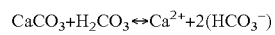

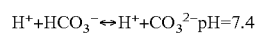

The buffer system is an $H_2CO_3/HCO_3^-$ buffer system in the antimicrobial cream, which keeps the cream at the proper pH.

Types of Bonds in the Antimicrobial Cream:

Several types of bonds are present in the antimicrobial cream of the present disclosure (1) Pauling bond in $SiO_4$; (2) ionic bonds; (3) hydrogen bonds; (4) Van der Waals bonds; (5) attractions between permanent dipoles and dipoles in induced nonpolar molecules; and (6) attractions between nonpolar molecules.

In some embodiments, the cream may be synthesized using a 3-phase process: (1) creating an anti-microbial colloid liquid, which may be blue; (2) creating an anti-microbial solid, which may be green; and (3) creating an anti-microbial, creamy, gelatinous solid and vitamin, which may be green. Mixing of the cream may be done with a mixer coated with a plastic material. This specific type of mixer may be needed because the skin cream is rich in mineral elements, trace elements, weak acids, and vitamins. Examples of each step are described below.

Example 1: Creating the Anti-Microbial Colloid Liquid 2.2 kg of salt were mixed in a phase manner with water. Sodium lauryl ether sulfate and 0.6 oz (or 18 g) of blue tartrazine were mixed in with the salt water, creating the anti-microbial colloidal solution having a blue color.

Example 2: Creating the Anti-Microbial Solid

The colloidal blue anti-microbial solution prepared in Example 1 was mixed with 25 L olive oil; 25 L clove oil; 20 L honey; 5 L green tea; 10 L aloe vera; a 260 kg mixture comprising kaolin gray, phyllosilicates, and aluminum silicate hydrates; 20 kg of talc; and 20 L of mineral oil. The solution was mixed thoroughly using a plastic coated blender, resulting in a green clay cream. It could have alternatively been mixed using just a plastic mixing spoon.

Example 3: Creating the Anti-Microbial, Creamy, Gelatinous Solid 95 kg of gelatin was slightly warmed to about 40° C. with 100 g of menthol to create a diluted solution. The amount of gelatin may be changed to change the viscosity of the skin cream. In embodiments, the gelatin may be added as a granular powder, which would swell when stirred into water. When dry gelatin is used, it may be used in an amount such that a water/gelatin mixture would not exceed about 34% gelatin. While warming, the gelatin solution may be allowed to hydrate for about 30 min. The diluted solution was poured into a mixing bowl. The green clay cream from Example 2 was then mixed into the mixing bowl. While the composition is being blended, it was simultaneously cooled to about 37° C. After cooling, vitamins are added to the mixture, which is then mixed again, creating antimicrobial green cream Kaolin clay, gelatinous and bright (the cream of the present disclosure).

The resulting cream includes silica, aluminum, calcium, and potassium as major elements and copper, lithium, molybdenum, and cobalt as minor elements. Some embodiments of the cream have a formula represented by $(Al,Zn,Fe_{1},67MgO_{33})Si_4O_{10}(OH)_2Na^+Ca^{2+}$ plus weak acids, such as benzoic acid, fatty acids, such as ascorbic acid, vitamins, and an antimicrobial agent. The mineral content of the product may vary due to the impurities.

The cream has anti-microbial and antibiotic properties and comprises trace elements, minerals, protein, polypeptides, and a weak acid, such as benzoic acid, which may give the cream its anti-aging and anti-microbial properties.

To use the cream of the present disclosure, a user may apply it externally on the skin or internally. When the cream is applied to the skin, transduction may occur, causing physical energy to be converted into energy used by the nervous system and reducing tension and anxiety in a user. For large wounds and burns, the cream may be gently rubbed on the wound or burn and covered with a compress when dry. The pain may be inhibited and the wound may heal without forming a scar. The cream may be removed from the body after the wound is healed by hydrotherapy, which may eliminate toxins.

The cream of the present disclosure may clean the skin of all or substantially all impurities, such as acne, spots, dead, skin fat, and the like. The cream may also have the ability to clean the face, heal most skin blemishes, whitlow, boils, ringworm, burns, stings, lesions, and the like. The cream may also be able to curb the proliferation of parasites, harmful bacteria, and microbes. The cream may also drain impurities, such as puss, from fabric, as the cream absorbs excess liquid and neutralizes the actions of various alkaloids. Moreover, the cream may have the ability to clean the blood and lymphatic system. The cream may also reinforce defenses, revitalize organs, neutralize poisons, strengthen bones, and reduce inflammation. In some embodiments, the cream may be used to nourish the scalp in cases of alopecia. Furthermore, the cream may help reduce or heal common hemorrhoid symptoms, including painless bright red blood from the rectum, anal itching, anal pain, tender lumps near the anus. Specifically, the cream of the present disclosure may have the ability to heal hemorrhoids in a maximum of about 3 or 4 days, wherein this may be possible due to the presence of coceth zinc sulfate, ZnO, and $TiO_2$.

Due to its composition, the cream of the present disclosure may ensure the use of physicochemical means of combating the presence and proliferation of microorganisms. Moreover, the cream has bactericidal, virucidal, fungicidal, and sporicidal properties due to its composition and ingredients.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A cream for treating the skin, the cream comprising:
   gray clay kaolin;
   sodium lauryl ether sulfate; $CH_3(CH_2)_{11}(OCH_2CH_2)_n OSO_3Na$, where n is from about 2 to about 3;
   blue tartrazine ($C_{16}H_9Na_3O_9S_2$);
   sodium chloride;
   menthol;
   metabisulfite sodium;
   gelatin;
   mineral oil;
   olive oil;
   oil of cloves;
   water;
   green tea;
   talc;
   honey; and
   aloe vera,
   wherein:
      a molecular structure of the cream includes an octahedral layer, an interlayer, and a tetrahedral layer.

2. The cream of claim 1, further comprising perfume.

3. The cream of claim 1, further comprising a mixture of vitamins.

4. The cream of claim 3, wherein the mixture of vitamins comprises vitamin E, vitamin C, vitamin B2, vitamin B5, vitamin H, vitamin B6, and vitamin D.

5. The cream of claim 1, further comprising apple perfume, vitamin E, vitamin C, vitamin B2, vitamin B5, vitamin H, vitamin B6, and vitamin D.

6. The cream of claim 5, wherein a batch of the cream comprises:
   about 260 kg gray kaolin clay;
   about 4 kg sodium lauryl ether sulfate;
   about 0.6 oz blue tartrazine;
   about 2.2 kg sodium chloride;
   about 100 g menthol;
   about 50 g metabisulfite sodium;
   about 95 kg gelatin;
   about 20 L mineral oil;
   about 25 L olive oil;
   about 25 L oil of cloves;
   about 20 L water;
   about 20 kg talc;

about 5 L green tea;
about ⅛ L perfume;
about 5 L honey;
about 10 L aloe vera;
about 2,000 international units (IU) vitamin E;
about 100,000 IU vitamin A;
about 300 mg vitamin C;
about 100 mg vitamin B2;
about 250 mg vitamin B5;
about 2.5 mg vitamin H;
about 100 mg vitamin B6; and
about 400 IU vitamin D.

7. The cream of claim 1, wherein the cream comprises about 60% gray clay kaolin.

8. The cream of claim 1, wherein the cream has a pH of about 7.4.

9. The cream of claim 1, wherein the cream comprises:
silica, aluminum, calcium, and potassium as major elements; and
copper, lithium, molybdenum, and cobalt as minor elements.

10. The cream of claim 1, wherein the cream comprises:
about 55 to about 65% by mass silicon;
about 7 to about 27% by mass aluminum;
about 10 to about 22% by mass iron; and
about 25% by mass of other oxides.

* * * * *